US009341680B2

(12) United States Patent
Ananth

(10) Patent No.: US 9,341,680 B2
(45) Date of Patent: May 17, 2016

(54) SELECTABLE UPPER VOLTAGE RANGE MONITORING CIRCUIT

(71) Applicant: Cameron Health, Inc., San Clemente, CA (US)

(72) Inventor: Ravi S. Ananth, Laguna Niguel, CA (US)

(73) Assignee: CAMERON HEALTH, INC., St. Paul, MN (US)

(*) Notice: Subject to any disclaimer, the term of this patent is extended or adjusted under 35 U.S.C. 154(b) by 324 days.

(21) Appl. No.: 14/067,266

(22) Filed: Oct. 30, 2013

(65) Prior Publication Data

US 2015/0115900 A1    Apr. 30, 2015

(51) Int. Cl.
H02J 7/34        (2006.01)
G01R 31/36       (2006.01)
A61N 1/39        (2006.01)
G01R 15/08       (2006.01)

(52) U.S. Cl.
CPC ............ *G01R 31/362* (2013.01); *A61N 1/3975* (2013.01); *G01R 15/08* (2013.01); *H02J 7/345* (2013.01)

(58) Field of Classification Search
CPC ..... G01R 31/3606; G01R 31/36; H02J 7/345; H02J 7/34
USPC ................................................ 320/166, 136
See application file for complete search history.

(56) References Cited

U.S. PATENT DOCUMENTS

| 4,259,639 | A | * | 3/1981 | Renirie | A61N 1/3708 324/426 |
| 4,276,883 | A | * | 7/1981 | McDonald | G01R 31/3648 607/29 |
| 4,556,061 | A | * | 12/1985 | Barreras | A61N 1/3708 320/136 |
| 6,185,454 | B1 | * | 2/2001 | Thompson | A61N 1/36 607/2 |
| 6,760,625 | B1 | * | 7/2004 | Kroll | A61N 1/3708 607/29 |
| 6,892,096 | B2 | | 5/2005 | Lyden | |
| 7,123,958 | B1 | | 10/2006 | Wong | |
| 7,239,146 | B2 | * | 7/2007 | James | G01R 19/16542 324/426 |
| 2010/0324618 | A1 | * | 12/2010 | Wanasek | A61N 1/3625 607/9 |
| 2011/0276103 | A1 | * | 11/2011 | Maile | A61N 1/36114 607/9 |
| 2015/0115900 | A1 | * | 4/2015 | Ananth | G01R 31/3606 320/166 |

* cited by examiner

Primary Examiner — Richard Isla Rodas
Assistant Examiner — Dung V Bui
(74) Attorney, Agent, or Firm — Seager, Tufte & Wickhem LLP

(57) ABSTRACT

A battery voltage measuring circuit for an implantable cardiac device is presented. Since the usable battery voltage for the device is limited to an upper range of voltages, the need for measuring lower voltages at which the battery is approaching end of life is of no use. The disclosed invention allows for the measurement of a selectable upper range of battery levels that can be chosen without using a level shifting device such as a zener diode. Multiple voltage ranges with associated measurement resolutions can be achieved without using high current zener diode implementations. This allows for a trade-off between measurement range and resolution while resulting in a lower power and more accurate measurement circuit. Conventional zener diode implementations only allow for a single measurement range and are prone to non-linear error as the voltage measurement range increases.

20 Claims, 4 Drawing Sheets

SELECTABLE UPPER VOLTAGE RANGE MONITORING CIRCUIT

BACKGROUND

Implantable medical devices are required to self-monitor their status for a variety of reasons. One status requirement is the battery voltage level to determine device lifetime left. Typically, the voltage on a lithium-manganese-dioxide battery, as with other battery chemistries, is fairly stable as long as the charge remaining in the battery is above a certain limit. The battery voltage ramps down rapidly, however, once the charge has been depleted beyond this limit. This makes most of the lower voltage range of a battery impractical for use, as very little battery life remains thereafter. As a result, only an upper range of a battery voltage is worth monitoring since the battery would be considered consumed or "dead" below the charge-limited voltage level. Since an analog-to-digital converter (ADC) with a limited number of bits is usually used to further process the measured voltage, limiting the voltage range of interest also allows for better resolution of the usable voltage instead of having the ADC operate over the entire battery voltage.

A common approach is to introduce a level shifting device, such as a zener diode, to eliminate the unneeded bottom voltage range from being measured. However, zener diodes provide a highly variable voltage level at low currents. To maintain a stable voltage, one must drive a zener diode with enough current (100 micro-amps or more) to reach a stable voltage portion on the zener's current-voltage curve. As the voltage across the battery being measured drops, however, this current level can also drop, again introducing variability. To avoid variability, added current margin is usually provided to keep the zener diode past the knee voltage.

In the field of implantable defibrillators, battery characterization must also accommodate the periodic reformation of high power capacitors for use in therapy delivery. Periodic reformation of therapy capacitors occurs at intervals (often one to three times yearly) to ensure the capacitors maintain desirable operating characteristics. Capacitor reformation is performed by putting the device in a high current state for a short period of time to charge the capacitors to a high voltage (several hundred volts or more). This high current operation depresses battery voltage for several days after it is performed in batteries commonly used in implantable systems.

To accommodate the depressed battery voltage after high current operations, designs may withhold battery measurement for a period of time (a number of days). However, to more effectively monitor battery status, it may be desirable to have, first, a narrow upper range of measurement for daily use, and a second broader range of measurement for use following the capacitor reformation.

Lower current consuming monitoring circuits with a high degree of stability are hence desired, which can allow for multiple voltage ranges to be accurately monitored.

OVERVIEW

The present invention provides a selectable boundary range for voltage monitoring that avoids the use of a level shifting zener diode, thereby reducing current consumption and improving resolution. In some illustrative examples, the circuit operates by introducing a controlled voltage reference for level shifting purposes. In some examples, the voltage reference for level shifting can be selectable to allow both narrow range and wide range monitoring. A voltage divider may be used to bring the battery voltage down to a level usable by the monitoring circuit which may operate at a lower voltage than the battery for example.

The following description is intended to provide an overview of the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
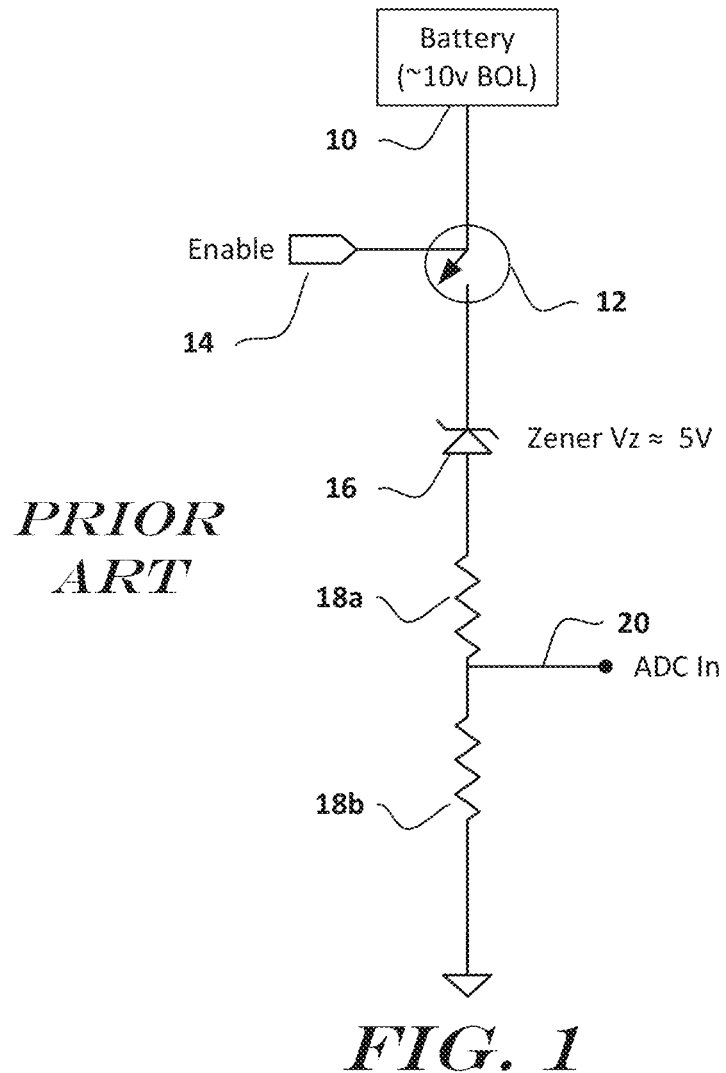
FIG. 1 is a simple prior art voltage monitoring circuit.

FIG. 1 is a simple prior art voltage monitoring circuit. In the illustrative circuit, the voltage of a battery 10 is to be measured. In the example, the battery 10 has a beginning of life open circuit voltage (BOL) of about ten volts, as indicated. A switch 12 enables the measurement to take place, and is controlled by an input signal "Enable", shown at 14. When enabled, the switch 12 closes and the battery biases the reverse biased zener diode 16 with a current determined by both the battery voltage and resistances (including voltage divider 18a/b) in the branch. In the example shown, the zener diode 16 has been chosen to have a voltage knee of about 5 volts with the resulting current obtained at battery BOL voltages. What this means is that the voltage drop across the zener diode 16 remains at 5 volts for a fairly wide range of currents. When the battery voltage drops, however, the biasing current decreases thereby decreasing the zener voltage. The level shifting voltage of the zener diode 16 is hence no longer constant at 5V over the range of battery voltages that are of interest.

The ADC 20 obtains a reading by digitizing the level-shifted and scaled battery voltage that was obtained from the voltage divider 18a/b to ground. In this example, when operating at BOL, for a desired level of zener bias current of 250 uA, one will need a resistance of (10V−5V)/250 uA=20 kOhms. The voltage divider 18a/b is scaled so that BOL creates the maximum voltage readable by the ADC. If however, the battery voltage drops to 7V, the resulting bias current will now drop to (7V−5V)/20 kOhms=100 uA. This in turn reduces the knee voltage of the zener diode which counteracts the reduction in current. As a result, the zener voltage will no longer be 5V, introducing error as the battery voltage decreases. For an implantable cardiac device, lower biasing currents and more linear measurement circuits are desired over the operational range of the battery.

Figure 2:
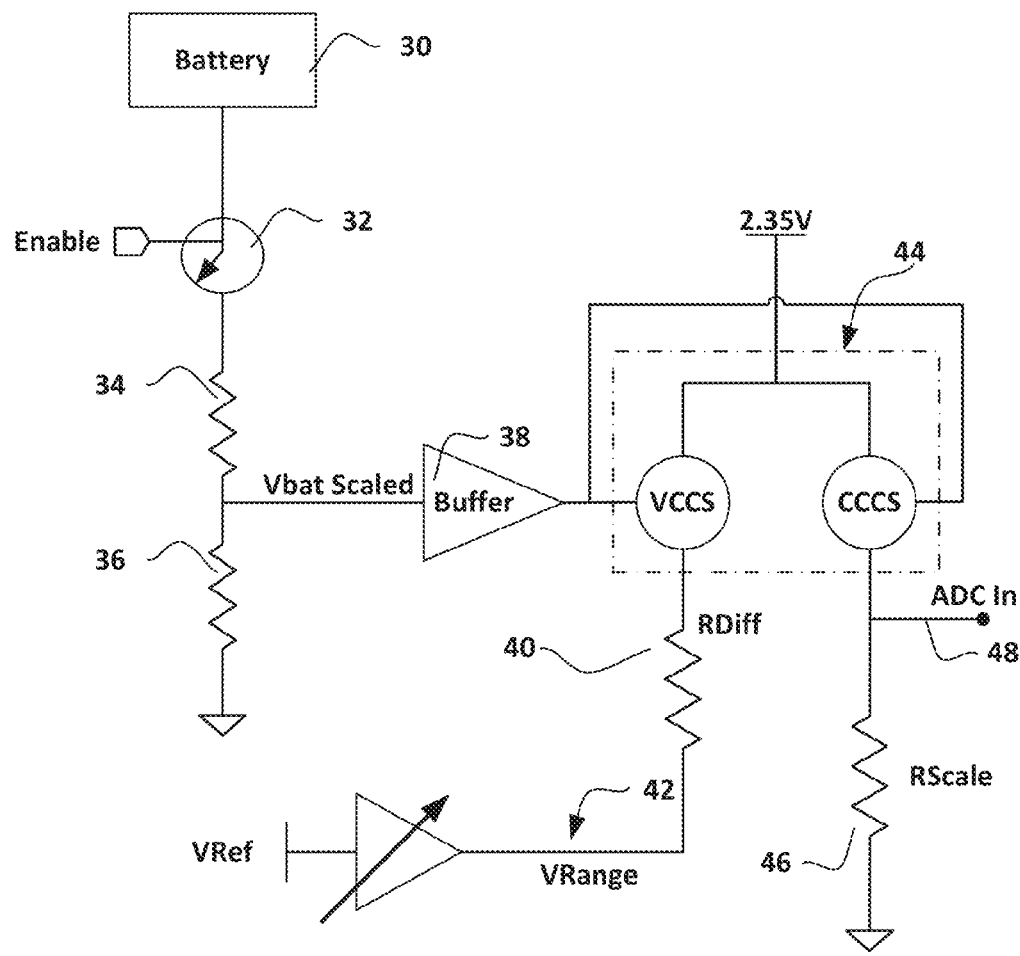
FIG. 2 is a block diagram for an illustrative embodiment.

FIG. 2 is a block diagram for an illustrative embodiment. In this illustrative example, current from a battery 30 goes through an enabling switch 32, and then to a voltage divider 34/36 referenced to ground, with a voltage VBatScaled taken off of the voltage divider 34/36. Here, the voltage divider 34/36 can have resistor values in the Mega-Ohm range since a zener diode does not have to be biased. This allows for a few micro-amps of the battery resulting in a drastic reduction in current drain.

The voltage divider that creates VbatScaled is made so that the battery's BOL creates the maximum voltage readable by the ADC. VbatScaled is fed to a voltage following amplifier 38, which applies the scaled voltage to the top of a resistor, RDiff 40 which in turn is not referenced to ground but rather to a scalable reference voltage, Vrange 42. The value of Vrange in turn is chosen such that VbatScaled equals Vrange when the battery voltage is at the lowest voltage level of interest. The amplifier/buffer 38 may have any suitable gain including that of a unity gain amplifier.

The amplifier/buffer 38, at unity gain, has current output determined by:

$$Iref = (VbatScaled - Vrange)/RDiff \qquad \text{Equation 1}$$

This reference current is used to create an output current mirror 44. The current mirror 44 drives current through a resistance, Rscale 46. The output is taken at 48, and preferably fed to an analog-to-digital conversion (ADC) circuit. In the illustrative example, the current mirror allows the reference current to be scaled as desired by a factor in, so that the output voltage to the ADC, ADCin 48 is:

$$ADCin = m*Iref*Rscale \qquad \text{Equation 2}$$

In the equation, the factor "m" is generated by the ratio of the widths of the transistors VCCS (the voltage controlled current source) and CCCS (the current controlled current source) within the current mirror 44. As an alternative, or in addition, Rscale can be selected to generate an output voltage that reflects the input battery voltage range being measured.

The output voltage fed to the ADC, ADCin, may then be summarized as being:

$$ADCin = Vdiff/Rdiff*m*Rscale \qquad \text{Equation 3}$$

Where Vdiff is equal to VbatScaled−Vrange, and 'm' is the current mirror scaling. As is evident from Equation 3, any of the various parameters can be changed to obtain the desired voltage range or resolution.

In the illustrative example, Vrange at 42 may be a selectable or scalable reference voltage, and the resistance Rscale at 46 may also be scalable. These selections allow multiple floating voltage ranges (i.e. not down to ground) to be measured with a desired resolution. From the floating range, the ADC can be used to digitize the relevant measurement. The separate ranges can be implemented without affecting the current drain off the battery 30.

In the working example, using an 8 bit ADC, the operating battery voltage ranges are 7.65V to 9.90 V giving a resolution of 8.8 mV in the fine mode, or 4.95 to 8.0 V for a resolution of 12 mV in the coarse mode. This means that the selectable Vrange 42 can be either 850 mV (fine resolution) or 550 mV (coarse resolution), with the voltage divider 34 set to divide VBat 30 by a factor of nine. In this working example, battery 30 is a three cell lithium-manganese-dioxide battery, having an initial open circuit voltage of about 9.9 V, such that the voltage VbatScaled 36 has a maximum of about 1.1 V. A Vrange of 850 mV gives a 250 mV voltage difference for fine resolution measurement while setting Vrange at 550 mV gives a voltage difference of 550 mV allowing for a wider range of battery voltage to be measured in a coarser measurement resolution for a fixed n-bit ADC.

Rdiff 40, in the working example, is 800 kilo-Ohms, such that the current through Rdiff 40 is under a micro-amp, even in the coarse range. The current through Rdiff 40 becomes a current reference and this is mirrored at the current mirror 44 which sinks the mirrored current through the selectable resistance, Rscale 46. Rscale 46 may be either 2 Mega-Ohms (coarse), or 3 Mega-Ohms (fine). Vrange 42 is buffered such that it can sink the needed current through Rdiff 40.

Other values may be used by manipulating the selectable Vrange 42 and resistance Rscale 46, as well as Rdiff and the voltage divider 34. If desired, multipliers may be included in the amplifier 38 and/or current mirror 44, using known methods. The specifics of the working example are intended for a particular application, and can be tailored by those skilled in the art.

In one embodiment, the implantable medical device is an implantable defibrillator, and uses periodic capacitor reformation on a stack of high power capacitors. The periodic capacitor reformation entails a high current draw from the battery, temporarily depressing the battery voltage, typically for several days. Following such reformation, VBat measurements may be made using the coarse measurement settings, to monitor the recovery curve following high current use, as this may be indicative of the battery's remaining capacity just as much as a lightly loaded or even open circuit voltage. Once the recovery reaches a defined level (i.e., no coarse step changes for two days, or at least 5-15 days have elapsed, for example), the device would revert to fine measurement settings.

One advantage of the circuit of FIG. 2 is that the Vrange voltage 42 can be taken from another, highly reliable voltage reference in the system. For example, rather than a reverse biased zener diode, a band gap reference may be used. The band gap reference may be divided or multiplied, as needed, to obtain desired levels. By adopting this approach, and excluding a zener diode, a more reliable, linear, and lower current implementation can be achieved.

Figure 3:
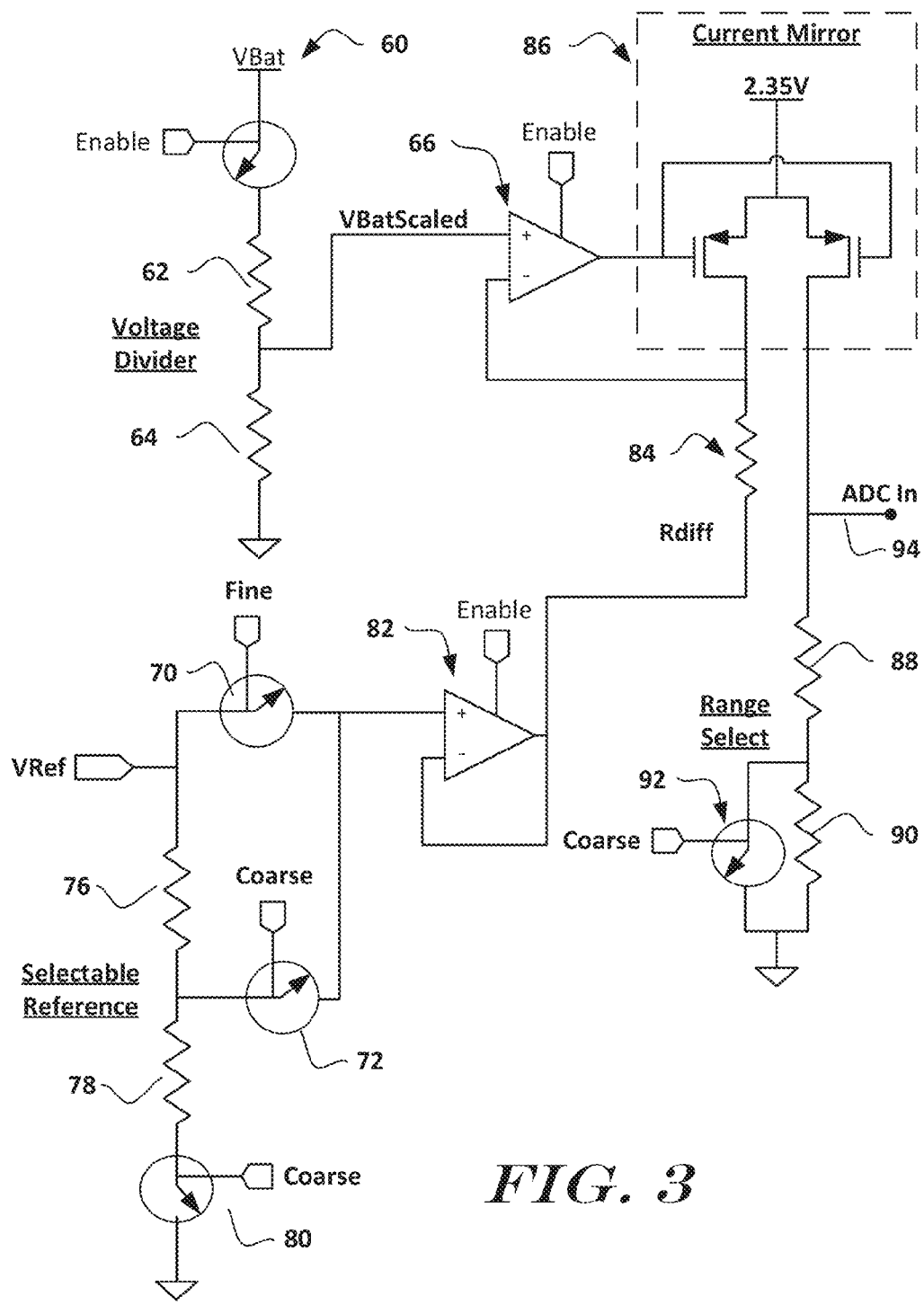
FIG. 3 is a circuit diagram for an illustrative embodiment.

FIG. 3 is a circuit diagram for an illustrative embodiment. In this example, the battery voltage 60 passes through an enabling switch to a voltage divider, shown with resistors 62, 64. The resulting divided voltage, VbatScaled is passed to an amplifier 66, which buffers the scaled voltage while creating a current reference that depends on the current passing through Rdiff. The current passing through Rdiff is determined by the values shown in Equation 1.

The current mirror 86 scales the reference current that passes through Rdiff 84 with the resulting voltage provided to the ADC being determined by the quantities in Equation 2. When the battery voltage is at the lowest voltage level of interest, Vdiff becomes zero, making the reference current through Rdiff and hence the mirrored current equal zero. This creates an ADCin 94 voltage of zero which is the intent. When the battery voltage is at the highest level of interest, Vdiff is at its maximum as well, raising the current through the range select circuit (resistors 88, 90 and switch 92) and increasing the voltage at ADCin 94.

The lower side of Rdiff is linked to a buffer 82, which takes a system reference voltage, Vref, scales it with a voltage divider and then buffers it to generates a voltage, Vrange that is applied to the bottom of Rdiff. In this example, the unscaled Vref voltage passes via switch 70 directly to the buffer 82 when a fine measurement is desired. When a coarse measurement is desired, Vref is scaled by voltage divider resistors 76, 78, as enabled by switch 80. Another switch 72 allows the scaled Vref to pass to the buffer 82, which sinks the current through Rdiff.

An output 94 is provided, preferably to an analog-to-digital (ADC) circuit. The output 94 is a product of the selectable resistance, Rscale 88/90 which is generated using either resistor 88 alone, or resistors 88 and 90 in series, depending on the state of switch 92.

In this circuit, the fine measurement takes place when switch 70 is closed, while switches 72 and 80 are open, to provide a larger reference voltage from buffer 82, and thereby reduced the voltage across Rdiff. In addition, switch 92 is open for the fine measurement, placing resistors 88, 90 in series and increasing the responsiveness at node 94 to changes in current through Rdiff. For a wider voltage range but coarser measurement, switches 72, 80 and 92 are closed, while switch 70 is open, providing a smaller voltage, Vrange at the output of the buffer 82. The voltage difference across Rdiff increases as a result, and, since switch 92 is closed, the voltage at node 94 is less responsive to changes in current through Rdiff, resulting in a coarser resolution for an ADC that processes the output at 94. The ADC that receives output 94 may use any conventional design.

Figure 4:
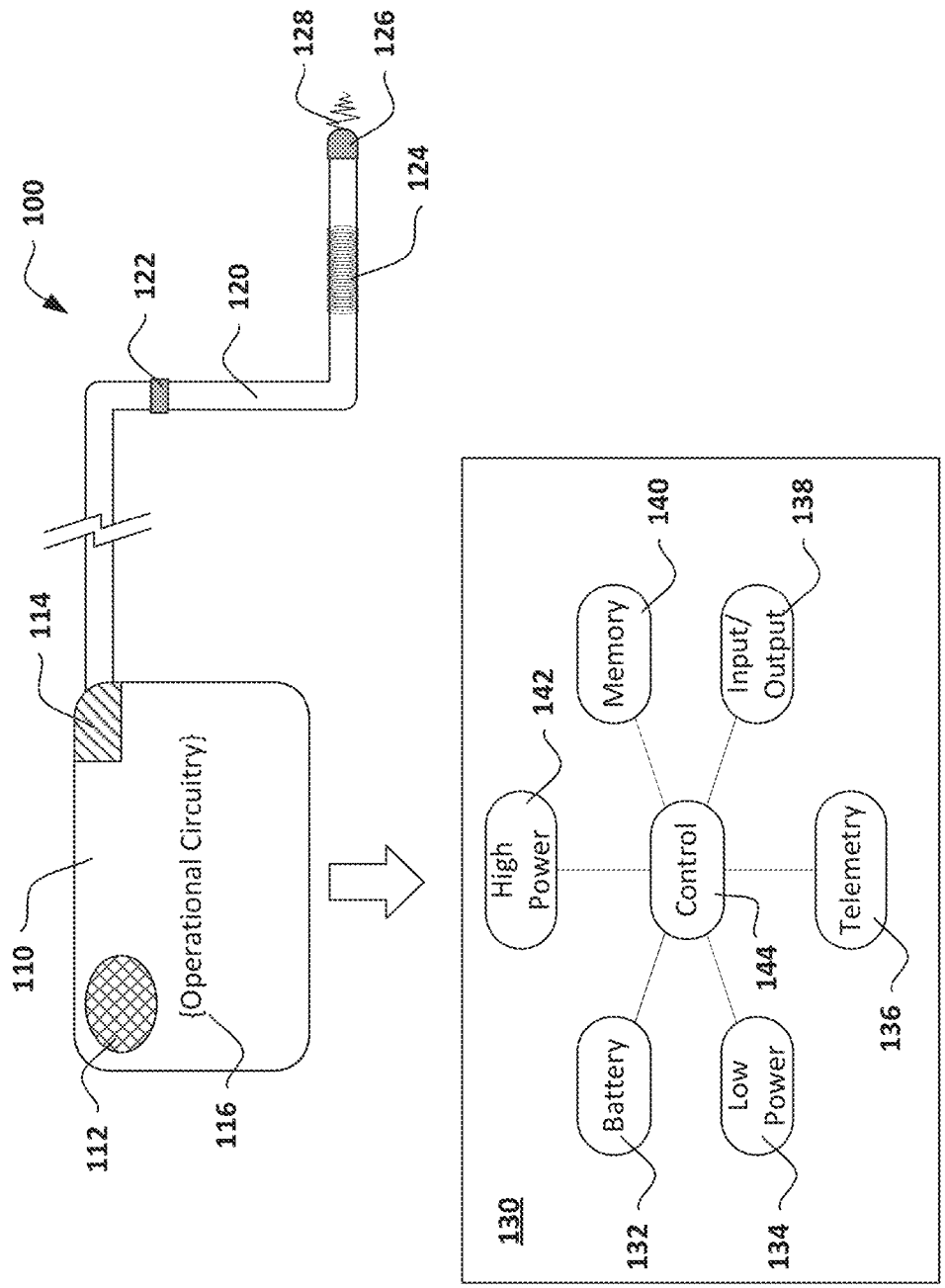
FIG. 4 illustrates an example implantable medical device.

FIG. 4 illustrates an example implantable medical device. The device is illustrated at 100 and includes a canister 110 and lead 120. Some illustrative features may include, for example, an electrode 112 on the canister 110 and a header 114 for coupling with the lead 120. The electrode 112 may be integral with the canister 110 or it may actually be the outer shell of the canister 110. The canister 110 will typically be a hermetically sealed unit that houses operational circuitry 116 for the implantable system 100.

The operational circuitry 116 may include various elements, and some illustrations are provided at 130. A battery is noted at 132. Most cardiac stimulation devices have non-rechargeable batteries, although some implantable devices are instead rechargeable. The present battery measurement embodiments may be used in systems using either rechargeable or non-rechargeable batteries. For a rechargeable battery, the outcome may indicate an estimated battery life and hence a time to initiate recharging. For a regular battery, the outcome may be to indicate an estimated battery status or a time for device replacement as it approaches its end of life.

The operational circuitry 116 usually includes some amount of low-power and mid-power circuitry 134 that can drive various functions including logic and processing, telemetry circuitry 136 with an RF radio, inductive telemetry or other technical solution (sonic, infrared, cellular) for communicating with a non-implanted external programmer, network or other device, input/output circuitry 138 for receiving, amplifying, filtering, etc. a biological signal or delivering a therapeutic output, memory 140 for storing instructions for operation as well as records of activity, observed events, treatment, status logs, etc. In addition, some devices include high power circuitry 142 such as the output circuitry for an implantable cardiac defibrillator. All of these elements 132-142 typically couple with one another via a control module 144 which may include a controller or processor. The present invention will typically be part of the low power circuitry 134.

The provision of each of a canister 110, with electrode 112 and header 114, and lead 120 with electrodes 122, 124, 126 and a distal attachment feature 128, as shown in FIG. 4, is merely illustrative. Other designs can also be used; for example, some implantable cardiac monitoring devices and/or so-called "seed" pacemakers have only a canister 110 and omit a lead 120. Some proposed systems include an elongated flexible housing, such as U.S. Pat. No. 6,647,292 (unitary subcutaneous defibrillator) or U.S. Pat. No. 7,734,343 (intravascular active medical implant), for example.

Some additional examples for hardware, leads and the like for implantable defibrillators may be found in commercially available systems such as the Boston Scientific Teligen® ICD and S-ICD® System, Medtronic Concerto® and Virtuoso® systems, and St. Jude Medical Promote® RF and Current® RF systems.

The various elements shown at 130 are not all required in any one system. For example, a device may use conducted emissions for communication, provided through the input/output circuitry 138 and omit the telemetry circuit 136 entirely. A lower power stimulus device may omit the high power circuit 142. A rechargeable device may include a recharge circuit (not shown) coupled to the power supply. Output circuits and high power circuitry 142 may be left out of an implantable loop recorder. The low power circuit 134 and control circuitry 144 may be combined. The indication that elements couple via control circuitry 144 is merely illustrated; in some instances the outer elements 132-142 may be directly connected together with control circuitry 144 simply controlling operation, rather than routing connections.

VARIOUS NOTES & EXAMPLES

A first example is an implantable cardiac device having a hermetic container including a battery coupled to operational circuitry for providing functionality to the implantable medical device. In this first example, the operational circuitry includes a battery monitoring circuit comprising the following: a voltage divider to generate a scaled voltage related to a battery voltage; a resistor, Rdiff, having first and second nodes; an amplifier having an output current and taking the scaled voltage and applying the scaled voltage to the first node of the Rdiff resistor; a level shifting reference voltage input coupled to the second node of the Rdiff resistor, such that the current through the Rdiff resistor is related to the difference between the scaled voltage and the level shifting reference voltage; a current mirror coupled to the output of the amplifier driving an output resistance, coupled such that the current mirror uses the current through Rdiff as a reference; and an output generating a battery voltage indicator coupled to the current mirror.

In a second example related to the first example, the amplifier is a unity gain amplifier. In a third example related to the first two examples, the voltage representative of the voltage output of the battery is generated using a resistive voltage divider circuit. In a fourth example related to the first three examples, the level shifting reference voltage is a selectable input having at least first and second voltage values.

In a fifth example related primarily to the fourth example, the output resistance is a selectable resistance having at least first and second resistance values. In a sixth example related primarily to the fifth example, the operational circuitry is configured to control each of the level shifting reference voltage and the output resistance to enable: a first battery voltage measurement range using the first voltage value for the level shifting reference voltage and the first resistance value for the output resistance; and a second battery voltage measurement range using the second voltage value for the level shifting reference voltage and the second resistance value for the output resistance.

In a seventh example related primarily to the sixth example, the operational circuitry further comprises an analog-to-digital converter sub-circuit for converting the battery voltage indicator to a digital value, such that the operational circuitry can convert the digital value depending upon whether the first battery voltage measurement range is enabled or the second battery voltage measurement range is enabled.

In an eighth example related primarily to the sixth example, the operational circuitry further comprises high power capacitors designed for delivery of defibrillation therapy, in which the operational circuitry is configured to perform high current operations to charge the high power capacitors either as part of periodic reformation of the capacitors or for therapy delivery purposes, wherein the operational circuitry is configured to use the first battery voltage measurement range by default, and to use the second battery voltage measurement range following a high current operation using the high power capacitors for a predetermined period of time.

In a ninth example related primarily to the sixth example, the operational circuitry further comprises high power capacitors designed for delivery of defibrillation therapy, in which the operational circuitry is configured to perform high current operations to charge the high power capacitors either as part of periodic reformation of the capacitors or for therapy delivery purposes, wherein the operational circuitry is configured to use the first battery voltage measurement range by default, and to use the second battery voltage measurement range following a high current operation using the high power capacitors until the battery voltage recovers after the high current operation.

In a tenth example related to any of the first nine examples, the operational circuitry further comprises an analog-to-digital converter subcircuit for converting the battery voltage indicator to a digital value. In an eleventh example related to any of the first ten examples, the level shifting reference voltage is generated without the use of a zener diode.

A twelfth example takes the form of a method of measuring battery voltage in an implantable cardiac device having a hermetic container including a battery coupled to operational circuitry for providing functionality to the implantable medical device. The operational circuitry in this twelfth example includes a battery monitoring circuit comprising the following: a voltage divider to generate a scaled voltage related to a battery voltage; a resistor, Rdiff, having first and second nodes; an amplifier having an output current and taking the scaled voltage and applying the scaled voltage to the first node of the Rdiff resistor; a level shifting reference voltage input coupled to the second node of the Rdiff resistor, such that the current through the Rdiff resistor is related to the difference between the scaled voltage and the level shifting reference voltage; a current mirror coupled to the output of the amplifier driving an output resistance, coupled such that the current mirror uses the current through Rdiff as a reference; and an output generating a battery voltage indicator coupled to the current mirror. The method of this twelfth example comprises: selecting a coarse or fine measurement mode for the battery voltage measurement by: selecting a reference voltage for the level shilling reference voltage, and selecting an output resistance; and measuring the battery voltage by: allowing current through the voltage divider, taking a voltage from the voltage divider using a buffer, creating a reference current through Rdiff, creating a current related to the current through Rdiff using the current mirror, and passing the related current through the output resistance to generate an output voltage providing a measure of the battery voltage.

A thirteenth example is related to the twelfth example and further comprises passing the measure of battery voltage to an analog-to-digital converter to digitize the battery measurement. A fourteenth example relates to either of the twelfth or thirteenth examples, in which the level shifting reference voltage is a selectable input having at least first and second voltage values.

A fifteenth example relates to any of the twelfth through fourteenth examples and is one in which the coarse measurement mode is selected by choosing a first reference voltage and a first output resistance; the fine measurement mode is selected by choosing second reference voltage and a second output resistance; the first reference voltage is smaller than the second reference voltage; and the first output resistance is smaller than the second output resistance.

A sixteenth example relates to any of the twelfth through fifteenth examples and is one in which the implantable medical device comprises high current circuitry capable of causing a high current event to take place; and the step of selecting a coarse or fine measurement mode is performed by determining whether a recent high current event in the implantable device has occurred and: if a recent high current event has occurred, selecting the coarse measurement mode; or otherwise, selecting the fine measurement mode.

A seventeenth example relates primarily to the sixteenth example and is one in which it is determined that a recent high current event has occurred if a high current event has taken place within a fixed period of time. An eighteenth example relates primarily to the sixteenth example and is one in which it is determined that a recent high current event has occurred if a high current event has taken place and, since the high current event, the battery voltage measured by the coarse mode has not been stable over consecutive measurements. A nineteenth example relates primarily to the sixteenth example and is one in which the implantable cardiac device comprises high power capacitors designed for delivery of defibrillation therapy, in which the a high current event includes charging of the high power capacitors for one of periodic reformation of the capacitors or for therapy delivery purposes. A twentieth example relates to any of the twelfth through nineteenth examples and is one in which the battery measurement is performed without the use of a zener diode.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMS), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An implantable cardiac device having a hermetic container including a battery coupled to operational circuitry for providing functionality to the implantable medical device, the operational circuitry including a battery monitoring circuit comprising the following:
   a voltage divider to generate a scaled voltage related to a battery voltage;
   a resistor, Rdiff, having first and second nodes;
   an amplifier having an output current and taking the scaled voltage and applying the scaled voltage to the first node of the Rdiff resistor;
   a level shifting reference voltage input coupled to the second node of the Rdiff resistor, such that the current through the Rdiff resistor is related to the difference between the scaled voltage and the level shifting reference voltage at the level shifting reference voltage input;
   a current mirror coupled to the output of the amplifier driving an output resistance, coupled such that the current mirror uses the current through Rdiff as a reference; and
   an output generating a battery voltage indicator coupled to the current mirror.

2. The implantable cardiac device of claim 1 wherein the amplifier is a unity gain amplifier.

3. The implantable cardiac device of claim 1 wherein the voltage representative of the voltage output of the battery is generated using a resistive voltage divider circuit.

4. The implantable medical device of claim 1 wherein the level shifting reference voltage is a selectable input having at least first and second voltage values.

5. The implantable cardiac device of claim 4 wherein the output resistance is a selectable resistance having at least first and second resistance values.

6. The implantable cardiac device of claim 5 wherein the operational circuitry is configured to control each of the level shifting reference voltage and the output resistance to enable:
   a first battery voltage measurement range using the first voltage value for the level shifting reference voltage and the first resistance value for the output resistance; and
   a second battery voltage measurement range using the second voltage value for the level shifting reference voltage and the second resistance value for the output resistance.

7. The implantable cardiac device of claim 6 wherein the operational circuitry further comprises an analog-to-digital converter sub-circuit for converting the battery voltage indicator to a digital value, such that the operational circuitry can convert the digital value depending upon whether the first battery voltage measurement range is enabled or the second battery voltage measurement range is enabled.

8. The implantable cardiac device of claim 6 wherein the operational circuitry further comprises high power capacitors designed fix delivery of defibrillation therapy, in which the operational circuitry is configured to perform high current operations to charge the high power capacitors either as part of periodic reformation of the capacitors or for therapy delivery purposes, wherein the operational circuitry is configured to use the first battery voltage measurement range by default, and to use the second battery voltage measurement range following a high current operation using the high power capacitors for a predetermined period of time.

9. The implantable cardiac device of claim 6 wherein the operational circuitry further comprises high power capacitors designed for delivery of defibrillation therapy, in which the operational circuitry is configured to perform high current operations to charge the high power capacitors either as part of periodic reformation of the capacitors or for therapy delivery purposes, wherein the operational circuitry is configured to use the first battery voltage measurement range by default, and to use the second battery voltage measurement range following a high current operation using the high power capacitors until the battery voltage recovers after the high current operation.

10. The implantable cardiac device of claim 1 wherein the operational circuitry further comprises an analog-to-digital converter subcircuit fix converting the battery voltage indicator to a digital value.

11. The implantable cardiac device of claim 1 wherein the level shifting reference voltage is generated without the use of a zener diode.

12. A method of measuring battery voltage in an implantable cardiac device having a hermetic container including a battery coupled to operational circuitry for providing functionality to the implantable medical device, the operational circuitry including a battery monitoring circuit comprising the following:

a voltage divider to generate a scaled voltage related to a battery voltage;

a resistor, Rdiff, having first and second nodes;

an amplifier having an output current and taking the scaled voltage and applying the scaled voltage to the first node of the Rdiff resistor;

a level shifting reference voltage input coupled to the second node of the Rdiff resistor, such that the current through the Rdiff resistor is related to the difference between the scaled voltage and the level shifting reference voltage at the level shifting reference voltage input;

a current mirror coupled to the output of the amplifier driving an output resistance, coupled such that the current mirror uses the current through Rdiff as a reference; and an output generating a battery voltage indicator coupled to the current mirror, the method comprising:

selecting a coarse or fine measurement mode for the battery voltage measurement by:

selecting a reference voltage for the level shifting reference voltage; and selecting an output resistance; and measuring the battery voltage by:

allowing current through the voltage divider, taking a voltage from the voltage divider using a buffer;

creating a reference current through Rdiff;

creating a current related to the current through Rdiff using the current mirror; and passing the related current through the output resistance to generate an output voltage providing a measure of the battery voltage.

13. The method of claim 12 further comprising passing the measure of battery voltage to an analog-to-digital converter to digitize the battery measurement.

14. The method of claim 12 wherein the level shifting reference voltage is a selectable input having at least first and second voltage values.

15. The method of claim 12 wherein:

the coarse measurement mode is selected by choosing a first reference voltage and a first output resistance;

the fine measurement mode is selected by choosing second reference voltage and a second output resistance;

the first reference voltage is smaller than the second reference voltage; and the first output resistance is smaller than the second output resistance.

16. The method of claim 12 wherein:

the implantable medical device comprises high current circuitry capable of causing a high current event to take place; and the step of selecting a coarse or fine measurement mode is performed by determining whether a recent high current event in the implantable device has occurred and:

if a recent high current event has occurred, selecting the coarse measurement mode; or otherwise, selecting the fine measurement mode.

17. The method of claim 16 wherein it is determined that a recent high current event has occurred if a high current event has taken place within a fixed period of time.

18. The method of claim 16 wherein it is determined that a recent high current event has occurred if a high current event has taken place and, since the high current event, the battery voltage measured by the coarse mode has not been stable over consecutive measurements.

19. The method of claim 16 wherein the implantable cardiac device comprises high power capacitors designed for delivery of defibrillation therapy, in which a high current event includes charging of the high power capacitors for one of:

periodic reformation of the capacitors or for therapy delivery purposes.

20. The method of claim 12, wherein the battery measurement is performed without the use of a zener diode.

* * * * *